United States Patent [19]
Mukerji et al.

[11] Patent Number: 5,707,968
[45] Date of Patent: Jan. 13, 1998

[54] INHIBITION OF ATTACHMENT OF H.INFLUENZAE TO HUMAN CELLS

[75] Inventors: Pradip Mukerji; Amanda Eun-Yeong Seo, both of Gahanna; Steven Neal Anderson, Pickerington; Linda Ann Harvey, Orient, all of Ohio

[73] Assignee: Abbott Laboratories, Abbott Park, Ill.

[21] Appl. No.: 734,792

[22] Filed: Oct. 23, 1996

Related U.S. Application Data

[63] Continuation of Ser. No. 249,556, May 26, 1994, abandoned.

[51] Int. Cl.$^6$ .............................. A61K 38/00; C07K 17/00
[52] U.S. Cl. .............................. 514/24; 514/12; 530/324; 530/350; 530/360; 530/361; 530/832; 424/535
[58] Field of Search .................. 514/21, 12; 530/324, 530/350, 360, 365, 832; 424/535

[56] References Cited

FOREIGN PATENT DOCUMENTS

| | | |
|---|---|---|
| WO 91/06308 | 5/1991 | WIPO . |
| WO 91/08675 | 6/1991 | WIPO . |
| 93/04171 | 3/1993 | WIPO . |
| WO9304172 | 3/1993 | WIPO . |
| 94/06306 | 3/1994 | WIPO . |
| 9532727 | 12/1995 | WIPO . |
| 9532728 | 12/1995 | WIPO . |
| 9627018 | 9/1996 | WIPO . |

OTHER PUBLICATIONS

Svanborg, et al., Adv. Exp. Med. Biol., 310:167–171 (1991).
Bakaletz et al., "Frequency of Fimbriation of Nontypable *Haemophilus influenzae* and it's Ability to Adhere to Chinchilla and Human Respiratory Epithelium", Infection and Immunity, 56(2):331–335 (1988).
Morse et al., "Haemophilus", Microbiology, 4th ed., Ed. by Davis et al., J.B. Lippincott Co., 615–618 (1990).
Harada et al., "Adherence of *Haemophilus influenzae* to nasal, nasopharyngeal and buccal epithelial cells from patients with otitis media", European Archives of Oto-Rhino-Laryngology, 247:122–124 (1990).
Anianson et al., "Anti-adhesive Activity of Human Casein Against *Streptococcus pneumoniae* and *Haemophilus influenzae*", Microbial Pathogenesis, 8:315–323 (1990).

Lönnerdal et al., "Cloning and Sequencing of a cDNA Encoding Human Milk B–casein", Federation of European Biochemical Societes Letters, 269(1):153–156.
Stephens et al., "Pathogenic Events During Infection of the Human Nasopharynx with *Niesseria meningitidis* and *Haemophilus influence*", Reviews of Infectious Diseases, 13:22–33 (1991).
Stenfors et al., "Abundant Attachment of Bacteria to Nasopharyngeal Epithelium in Otitis–Prone Children", Journal of Infecitous Diseases, 165: 1148–1150 (1992).
Takahashi et al., "Phosphorylation of a Surface Receptor Bound Urokinase–Type Plasminogen Activator in a Human Metastatic Carcinomatous Cell Line", Biochemical and Biophysical Research Communications, 182 (3):1466–1472 (1992).
Sheard, "Breast Feeding Protects Against Otitis Media", Nutrition Reviews, 51(9):275–277 (1993).
Duncan et al., "Exclusive Breast Feeding for at Least 4 Months Protects Against Otitits Media", Pediatrics, 91(5):867–872 (1993).
Hansson et al., "Expression of Human Milk β–Casein in *Escheria coli*; Comparison of Recombinant Protein with Native Isoforms", Protein Expression and Purification, 4:373–381 (1993).
Ardehali et al., "Indium Labeling of Microorganisms to Facilitate the Investigation of Bacterial Adhesion", Journal of Biomedical Materials Research, 27:269–275 (1993).

*Primary Examiner*—Cecilia J. Tsang
*Assistant Examiner*—Abdel A. Mohamed
*Attorney, Agent, or Firm*—Cheryl L. Becker; Thomas D. Brainard

[57] ABSTRACT

The attachment of *H. influenzae* to human cells, such as oropharyngeal cells, may be inhibited by native human β-casein, a recombinant form of human β-casein, and hydrolysates of both. The human β-casein or hydrolysate may be contained in a liquid enteral nutritional product such as an infant formula. The enteral nutritional product may be used, for example, in the prevention and treatment of otitis media in infants. The human β-casein or hydrolysate may also be administered as a throat spray or nasally using drops or a spray.

6 Claims, No Drawings

INHIBITION OF ATTACHMENT OF H.INFLUENZAE TO HUMAN CELLS

This application is a Continuation of application Ser. No. 08/249,556, filed on May 26, 1994 now abandoned.

The present invention relates generally to inhibiting the attachment of *Haemophilus influenzae* to human cells, and more specifically to the use of native or recombinant human β-casein and hydrolysates thereof for inhibiting the attachment of *Haemophilus influenzae* (*H. influenzae*) to human cells.

Haemophilus are small, gram-negative, non-motile, non-spore forming bacilli with complex growth requirements. Diseases caused by *H. influenzae* usually begin as a nasopharyngitis, possibly precipitated by a vital infection of the upper respiratory tract. Morse, et al. "Haemophilus", *MICROBIOLOGY FOURTH EDITION*, published by J. B. Lipincott Company, pages 615–618 (1990).

*H. influenzae* are spread from person to person by airborne respiratory droplets or direct contact with secretions. To colonize, *H. influenzae* must contend with ciliary clearance mechanisms of the nasopharyngeal mucosal surface and the mucous barrier. Once past the mucous barrier and the ciliary escalator, *H. influenzae* attach to mucosal epithelial cells. Invasion of mucosal surfaces appears to be an important characteristic of pathogenic bacteria. Stephens, et al., "Pathogenic Events During Infection of the Human Nasopharynx with *Neisseria meningitis* and *Haemophilus influenzae*", REVIEWS OF INFECTIOUS DISEASES, 13:22–23 (1991). It has further been reported that *H. influenzae* harbored in the nasopharynx are a key factor in the development of middle ear infections (otitis media), and that non-typable *H. influenzae* adhere to nasopharyngeal and nasal mucosal cells. Harada et al., "Adherence of *Haemophilus influenzae* to nasal, nasopharyngeal and bucal epithelial cells from patients with otitis media" *EUROPEAN ARCHIVES OF OTO-RHINO-LARYNGOLOGY*, 247:122–124 (1990). Stenfors et al., "Abundant Attachment of Bacteria to Nasopharyngeal Epithelium in Otitis-Prone Children", *THE JOURNAL OF INFECTIOUS DISEASES*, 165:1148–1150 (1992). In accordance with the present invention β-casein isolated from human milk or a recombinant form thereof, or a hydrolysate of either is employed to inhibit the adhesion of *H. influenzae* to human cells.

Exclusive breast-feeding of human infants for the first four months of life has been associated with a decrease in the incidence of both acute and recurrent otitis media. However, the question remained as to whether it is breast milk per se or the mechanics of breast feeding that exert the protective effect. Sheard, "Breast-Feeding Protects Against Otitis Media", *NUTRITION REVIEWS*, Vol. 51, No. 9, pages 275–277 (1993). In one study of 1,013 infants followed for their entire first year, 47% had at least one episode of otitis media and 17% had recurrent otitis media. Infants exclusively breast fed for four or more months had half the mean number of acute otitis media episodes as those not breast fed at all and 40% less than those infants whose diets were supplemented with other foods prior to four months. The recurrent otitis media rate in infants exclusively breast-fed for six months or more was 10% and was 20.5% in those infants breast-fed for less than four months. Those investigators presented speculations that IgA, or micronutrients or Prostaglandin E, in breast milk may be protective, but concluded that the mechanism for a protective effect of breast-feeding against otitis media was not clear. Duncan et al., "Exclusive Breast-Feeding for at Least 4 Months Protects Against Otitis Media", *PEDIATRICS*, Vol. 91, No. 5, pages 867–872 (1993).

WO 91/06308 filed by Andersson et al. for "ANTIBACTERIAL COMPOSITION", and a published article by the same authors (Aniansson et al., "Anti-adhesive activity of human casein against Streptococcus pneumonia and *Haemophilus influenzae*", *MICROBIAL PATHOGENESIS*, 8:315–323 (1990) disclose the use of a milk fraction having a molecular weight of at least 5,000 daltons for "therapeutic prophylactic, and/or diagnostic use in infections caused by *S. pneumonae* and/or *H. influenzae*", but it is suggested in these publications that the beneficial effect is provided by kappa-casein. However, the present invention relates to the use of native or recombinant human β-casein and hydrolysates of both to inhibit *H. influenzae* infections.

WO93/04172 relates to a DNA sequence encoding human β-casein, but does not disclose the capacity of either native or recombinant human β-casein to inhibit the attachment of *H. influenzae* to human cells.

WO91/08675 discloses an infant formula which contains recombinant forms of both human alpha-lactalbumin and human β-casein. However, this publication discloses only that these human milk proteins will "give a simulated human mother's milk formula that does not exhibit the allergenic properties associated with formulas based on cow or other foreign protein." (page 3, lines 20–22). The use of human β-casein to inhibit the attachment of *H. influenzae* to human cells is not taught or suggested in said publication.

The two assays (a radiolabeled assay and an ELISA assay) which were used for determining the bioactivity of β-casein are described below. These assays have not been published heretofore, although the ELISA assay was based upon established methodology.

MATERIALS USED IN BOTH ASSAYS

*Haemophilus influenzae*

*Haemophilus influenzae* (*H. influenzae*) cultures (fimbriated, nontypable) which have been implicated in otitis media were obtained from Dr. Lauren Bakeletz of The Ohio State University, Columbus, Ohio, U.S.A. The use of these organisms in assays has been described in Bakaletz, et al., "Frequency of Fimbriation of Nontypable *Haemophilus influenzae* and its Ability to Adhere to Chinchilla and Human Respiratory Epithelium", *Infection and Immunity*, 56: 331–335 (1988). The *H. influenzae* were streaked onto Chocolate agar plates (BBL-Becton Dickinson & Co., Cockeysville, Md., U.S.A.) from frozen aliquots of a low passage number and incubated at 37° C. in a 5% $CO_2$ incubator for about 18 hours to obtain logrithmically growing cultures. The *H. influenzae* was used in both the Enzyme Linked Immuno Sorbent Assay (ELISA) assay and the radiolabeling assay as described below.

Native Human β-Casein

β-casein isolated from human milk was purchased from Symbicom AB, P.O. Box 1451, S-901 24 Umea, Sweden.

Recombinant Human β-Casein

Applicants obtained β-casein cDNA and the expression system from Symbicom AB, P.O. Box 1451, S-901 24 Umeå, Sweden. The human β-casein cDNA used had been previously cloned and sequenced by Lonnerdal et al., Cloning and sequencing of a cDNA encoding human milk β-casein. (SEQ ID NO: 1:) *Federation of European Biochemical Societies Letters* 269, 153–156 (1990). The recombinant human β-casein was obtained from *E. coli* and purified according to the method of Hansson et al., Expression of Human Milk β-Casein in *Escherichia coli*: Comparison of Recombinant Protein with Native Isoforms. *Protein Expression and Purification* 4, 373–381 (1993). To express human β-casein in *E. coli*, β-casein cDNA was cloned under control of a T7 promoter in two different expression vectors, One vector, pS26, was designed for intracellular expression. The other vector, pS28, has a signal sequence for extracellular expression. The procedure followed was substantially that described by Hansson et al.

Human β-casein cDNA was isolated by Hansson et al, as a 1.1-kb EcoRI fragment from a human lambda gt mammary gland library, and was subcloned into pUC19, which was designated pS21. The cDNA was modified by introduction of synthetic oligonucleotides in the 5' and 3' termini. To introduce a suitable cloning site in the 5' end, NdeI, a translational start, was inserted in front of the sequence encoding mature human β-casein. To adapt the initial part of the translated sequence to *E. coli* codon usage, six synthetic oligonucleotides were constructed and ligated. Also, PstI and EcoRI sites were inserted in front of the NdeI site, The sequence of the synthetic fragment was 5'-CTGCAGAATTCAT<u>ATGCGT</u> GAAACCATCGAATC-CCTGAGCTCGAGCGAAGAATCGATCAC-CGAATACAAAAAGTTGAAAAAGTTAAACACG AGGACCAG GATCC-3'. (SEQ ID NO: 2:) The protein encoding sequence is underlined. The synthetic fragment was cloned into PstI/BamHI-digested pUCIg resulting in plasmid pS24. To insert the rest of the β-casein encoding sequence, a 303-bp AccI/BglII fragment was isolated and cloned into a pUC18 derivative and designated plasmid pS22. Four synthetic oligonucleotides containing the sequence encoding the carboxy-terminal end and translation stop followed by BamHI and EcoRI sites were constructed resulting in the sequence 5'<u>AGATCTACCCTGTGA CTCAGCCACTTGCCCCAGTTCATAACCCCATTAGT-GTCTAATAAGGATCCGAATTC</u>-3', (SEQ ID NO: 3:) where the protein encoding sequence is underlined. The synthetic fragment was cloned into BglII/EcoRI digested pS22, resulting in plasmid pS23. To obtain the recombinant modified β-casein encoding fragment, three fragments were ligated: an 89-bp PstI/AvaII fragment from pS24; a 197-bp AvaII/AccI fragment from pS21; and PstI/AccI digested pS23. The resulting plasmid pS25 was digested with NdeI/BamHI and a 641-bp fragment was isolated and cloned into the vector pET-3a. The resulting expression vector was designated pS26.

In order to construct a vector mediating extracellular expression, the *E. coli* signal sequence of the enterotoxin STII gene was introduced in front of the β-casein encoding sequence. A modified STII sequence with NcoI- and NdeI-compatible ends and an internal ClaI site was obtained by using a synthetic oligonucleotide, 5'-CATGAAAAAGAATATCGCATTTCTTCTTGCATC-GATGTTCGTTT TTTCTATTGCTACAAATGCATATG-3' (SEQ ID NO: 4:). To insert the signal sequence in front of the β-casein encoding sequence, pS25 was digested with AvaI/EcoRI and a 619-bp fragment was isolated. This fragment was ligated with a synthetic oligonucleotide fragment, 5'CATATGCACGTGAAACCATCGAATCCCTGAGCT-CGAG-3' (SEQ ID NO: 5:), and NdeI/EcoRI-digested pUC19. The resulting plasmid was designated pS27. The final expression vector,pS28, was constructed by ligating three fragments: a 700-bp NdeI/HindIII β-casein fragment isolated from pS27, the STII signal sequence, and a NcoI/HindIII-digested pACAT7 vector.

The expression vectors pS26 and pS28 were used to transform *E. coli* strains BL21(DE3), BL21(DE3)pLysS, and BL21(DE3)pLysE. The bacteria were grown in Luria Broth medium containing 50 µg/ml carbenicillin, and when Bl21(DE3)pLysS and BL21(DE3)pLysE were used the medium was supplemented with 25 µg/ml chloramphenicol.

For induction of expression the cultures were grown to a density yielding an optical density (OD) of 0.6 at a wavelength of 600 nanometers ($OD_{600}$), then 0.4 mM IPTG was added to induce the T7 system. The cells were harvested about 90 minutes after induction.

Recombinant β-casein was isolated using standard procedures. The inducible T7-based expression system resulted in high-level expression of recombinant β-casein. Bacteria were harvested and the cells pelletted by centrifugation. The supernatant contained the periplasmic proteins and the pellet the cytoplasmic fraction. The recombinant proteins obtained were compared with native β-casein, which had been purified by standard methods including either ion-exchange chromatography followed by reversed-phase HPLC or gel filtration. Recombinant and native β-casein were compared by standard biochemical techniques comprising SDS-PAGE, Western blotting, amino acid analysis, peptide mapping, phosphate analysis, and mass spectrometry. Recombinant β-casein expressed in *E. coli* was found to comigrate with full-length, nonphosphorylated native human β-casein, which is one of seven native isoforms.

Recombinant human β-casein has also been expressed in *S. cerevisiae* using the pYES 2.0 vector (Invitrogen Corp., San Diego, Calif.), but the expression level was approximately 10% of that obtained in *E. coli*. However, Hansson et al. found that *S. cerevisiae* appeared to express phosphorylated human milk β-casein.

β-Casein Hydrolysates

The human β-casein (both native and recombinant) was digested using the specific endoproteinase GLU-C (Sigma, sequencing grade) which catalyzes the hydrolysis of peptide bonds at the C-terminal of glutamic acid residue. After monitoring the digest using high pressure liquid chromatography, an enzyme to protein ratio of 1:100 (weight/weight) was chosen for a 30 hour digestion at 37° C. in 0.1M $NH_4HCO_3$, pH 7.8. These digests were dried and resuspended in appropriate buffers prior to use in the assays discussed above.

RADIOLABELED ASSAY

Detroit 562 cells

Detroit 562 pharyngeal carcinoma cells were obtained from the American Type Culture Collection (Rockville, Md., U.S.A.). The use of this type of cell in assays has been described in Takahashi, et al. "Phosphorylation Of A Surface Receptor Bound Urokinase-Type Plasminogen Activator In a Human Metastatic Carcinomatous Cell Line", *BIOCHEMICAL AND BIOPHYSICAL RESEARCH COMMUNICATIONS*, 182:1466–72. The Detroit 562 cells were cultured in Dulbecco's Modified Eagle Medium (GIBCO, Grand Island, N.Y., U.S.A.) supplemented with 10% Fetal Bovine Serum (Hyclone, Logan, Utah. U.S.A.) Cells were routinely subcultured in 75 $cm^2$ flasks (Costar, Cambridge, Mass., U.S.A.) using Trypsin-EDTA (0.25% trypsin, 1 mM EDTA (Ethylenediaminetetraacetic acid), (GIBCO) to detach cells. Cell subculture passages 48–75 were utilized for adhesion studies. Cells were seeded into 96 well plates (Costar) at a density of 20,000 cells per well and maintained at 37° C. in a 5% CO2 incubator for 8–10 days providing a confluent monolayer for adhesion studies. Plates were washed three times with 200 µl Hanks Balanced salt solution (HBS) (GIBCO), supplemented with 30 mM of N-2-Hydroxyethylpeperazine-N'-2-Ethane Sulfonic Acid (HBS) (GIBCO) to remove serum proteins, before addition of bacteria in adhesion assays.

Radiolabeling of bacterium

Harvested bacteria in phosphate buffered saline supplemented with 0.05% Bovine serum albumin (PBS-BSA) were centrifuged and resuspended in a volume of PBS-BSA yielding an optical density (OD) of 2.4 at a wave length of 600 nanometers ($OD_{600}$). $^{111}$-Indium-oxine ($^{111}$-In) (Amersham, Arlington Heights, Ill., U.S.A.) a high energy, short lived tracer, was utilized to radiolabel the bacteria. (The $^{111}$-In penetrates the cell membrane, where once inside the cell it dissociates resulting in the binding of $^{111}$-Indium ions with cytoplasmic components.) The use of $^{111}$-In labeling in other assays has been described in Ardehali, et al. "$^{111}$-Indium Labeling of Microorganisms to Facilitate the Investigation of Bacterial Adhesion", JOURNAL OF BIO-MEDICAL MATERIALS RESEARCH, 27: 269–275 (1993). 50 µCi of an $^{111}$-In solution was added to 2.5 ml of the bacterial suspension at 37° C. and incubated for 20 minutes. The radiolabeled bacteria were then washed two times and resuspended in 5 ml HBS supplemented with 30 mM HEPES buffer. 25 µl of the $^{111}$-In labeled bacterial suspension were preincubated with 25 µl of β-casein in a polypropylene 96 well plate for 15 minutes at 37° C. to allow binding of β-casein to bacteria.

Table 1, human β-casein exhibited an inhibition of 50% or more at concentrations of 0.75 mg/ml or greater. It should be noted than when referring to Table 1, a higher percent inhibition indicates a higher level of bioactivity of the "AGENT", and a lower percent inhibition indicates a lower level of activity of the "AGENT". Bovine β-casein was not significantly active even at 1.5 mg/ml. These results indicated that casein from human milk has different bioactivity compared to the bovine milk β-casein.

Hydrolysate of human β-casein obtained with GLU-C enzyme (prepared as described above) was also active (>50% inhibition) at concentrations of 0.75 mg/ml or higher. When the GLU-C hydrolysate of purified recombinant β-casein was tested at 3.0 mg/ml, it exhibited activity similar to that of the human milk β-casein hydrolysate. Hence, this recombinant protein could be produced in large-scale from bacteria to provide an abundant supply of a protein which retains the anti-adhesion activity of native human milk β-casein against H. influenzae.

TABLE 1

PERCENT INHIBITION OF H. influenzae ATTACHMENT TO DETROIT 562 CELLS

| AGENT | CONCENTRATION NG/NL | EXP 1 | EXP 2 | EXP 3 | AVERAGE |
|---|---|---|---|---|---|
| β-Casein Isolated from Human Milk | 3 | 67 | ND* | ND* | 67 |
| | 1.5 | 71 | 34 | 45 | 50 |
| | 0.75 | 60 | ND* | ND* | 60 |
| | 0.5 | ND* | 27 | 28 | 28 |
| Hydrolysate of β-Casein Isolated from Human Milk | 3 | 60 | | | |
| | 1.5 | 51 | | | |
| | 0.75 | 52 | | | |
| Recombinant Human β-Casein Hydrolysate | 3.0 | 71 | | | |
| Bovine β-Casein | 1.5 | 31 | | | |
| | 0.5 | 24 | | | |

*ND = NOT DONE

Radiolabeled bacterial adhesion measurement

25 µl of the preincubation mixture containing both radiolabeled bacteria and β-casein was pipetted into each well of the assay plate containing Detroit 562 cells. The assay plate was incubated for 20 minutes at 37° C. to allow adhesion of the bacterium to the cell monolayer. The plates were then washed three times with HBS to remove nonadhering bacteria from the Detroit 562 cells. The assay was terminated by the addition of 100 µl of 1N sodium hydroxide (NaOH) to disrupt the cell monolayer. The entire contents of each well was placed in a Cobra polypropylene tube (12 mm in diameter and 75 mm in height) (Packard, Meriden, Conn., U.S.A.) and counted on a Cobra gamma counter (also from Packard). Results were calculated by averaging the results of four replicates after the subtraction of background radiation. Results are presented as percent inhibition of bacterial attachment in no agent control wells.

RESULTS FROM RADIOLABELED ASSAY

The human and bovine β-casein solutions were prepared first in 20 mM ethanolamine, 6M urea, pH 9.5 and then washed twice in PBS by ultrafiltration using Centricon membrane filters (Amicon, Mass.) with a cut-off of 3,000 daltons. After resuspending in appropriate buffer for the radiolabeled assay described above, these samples were tested in the assay. Experiments with different designated numbers were performed in different days. As shown in ELISA ASSAY H. influenzae Preparation Harvested H. influenzae from chocolate agar plates were suspended in 7 ml PBS-BSA and biotinylated by incubation with 350 µl of biotin-caproate N-hydroxysuccinimide ester (0.01 g biotin/1 ml dimethyl sulfoxide; Sigma, St. Louis, Mo., U.S.A.) for 15 minutes at room temperature. The biotinylated bacteria were washed three times at 2,700 rpm for 30 minutes each to remove excess biotin. The labeled bacteria were then resuspended at an $OD_{600}$ of 2.4 using PBS-BSA.

Oropharyngeal cells

Oropharyngeal (OP) cells were collected from donors and pooled in phosphate buffered saline (PBS). Cell suspensions washed one time in PBS were resuspended and counted using a hemocytometer. Cells were adjusted to a density of $2.5 \times 10^5$ cells per ml in PBS. To promote OP cell attachment, 96-well plates (Linbro-ICN, Costa Mesa, Calif., U.S.A.) were coated with L-lysine followed by exposure to 1.25% glutaraldehyde (creates cross-linking). Plates were thoroughly washed to remove any residual glutaraldehyde. Each well of the 96-well plate was inoculated with 50 µl of the OP cell preparation yielding a final concentration of $1.25 \times 10^4$ cells per well. Designated wells were incubated with PBS only (no OP cells) to serve as background control wells to measure non specific bacterial binding to plastic. Inoculated plates were centrifuged at 2,700–3,000 rpm for ten minutes to sediment the suspended cell preparation, aspirated and incubated overnight at 37° C. in a moist chamber. The next morning plates with OP cells were treated with PBS containing 5% BSA for four hours to prevent non-specific bacterial attachment. The plates were washed three times with 200 µl PBS-BSA before use in adhesion assays.

these results indicated that the recombinant human β-casein, human milk β-casein and its hydrolysate inhibit attachment of H. influenzae to normal human oropharyngeal cells as well as human tumor cells.

TABLE 2

PERCENT INHIBITION OF H. influenzae ATTACHMENT TO HUMAN OROPHARYNGEAL CELLS

SET I

| AGENT | CONCENTRATION NG/NL | EXP 1 | EXP 2 | EXP 3 | EXP 4 | EXP 5 | AVERAGE |
| --- | --- | --- | --- | --- | --- | --- | --- |
| β-Casein Isolated from Human Milk | 0.5 | 10 | 45 | 56 | 45 | 31 | 37 |
| Recombinant Human β-Casein | 0.5 | 49 | 58 | 53 | 40 | | 50 |
| Bovine β-Casein | 0.5 | 0 | 0 | 0 | 0 | 0 | 0 |

SET II

| AGENT | CONCENTRATION NGINL | EXP 1 | EXP 2 | EXP 3 | AVERAGE |
| --- | --- | --- | --- | --- | --- |
| β-Casein Isolated from Human Milk | 1 | 53 | 88 | 68 | 70 |
| | 0.5 | 12 | ND* | 82 | 47 |
| | 0.25 | 20 | ND* | ND* | 20 |
| Hydrolysate of β-Casein Isolated from Human Milk | 1 | 70 | 48 | | |
| | 0.5 | | 73 | | |

*ND = Not Done

Adhesion Measurement

The biotinylated H. influenzae were diluted 1:1 with β-casein or control buffer (PBS-BSA) and incubated at 37° C. in a shaking water bath for 30 minutes. 50 µl of the preincubation mixture was placed into the appropriate well of the OP cell assay plate and incubated for 60 minutes at 37° C. The assay was halted by washing the assay plates three times with PBS-BSA and the plate heat fixed at 65° C. for 10 minutes. After the plate cooled to room temperature, 100 µl of Extravidin-peroxidase conjugate (Sigma), diluted 100-fold in PBS-BSA, was added to each well and the plate incubated for 40 minutes at 37° C. This conjugate binds to the biotin-labeled bacteria. Excess unbound conjugate was removed by washing the assay plate three times with PBS-BSA and 100 µl of peroxidate substrate 2,2'-Azino-bis(3-Ethylbenzthiazoline-6-Sulfonic Acid) was added to each well. Plates were incubated for 10 minutes and subsequently monitored for color development on a Thermomax 96 well plate reader (Molecular Devices, Menlo Park, Calif., U.S.A.) until the positive control wells containing OP cells and biotinylated bacteria (no β-casein) reached an $OD_{600}$ of 2.5 to 3.0. Binding results were calculated by averaging the results of three replicates.

RESULTS FROM ELISA ASSAY

Since the Detroit 562 cells were derived from a pharyngeal tumor, the proteins described in Table 1 were also tested in an anti-adhesion assay with normal human oropharyngeal cells from volunteers. Results from this ELISA assay are shown in Table 2. Once again, native human milk β-casein and recombinant human β-casein were found to be active at 0.5 mg/ml while bovine β-casein was inactive in the experiments described in SET I. After the analysis of the readings was adjusted for maximum sensitivity of the assay, human β-casein and its GLU-C hydrolysate were still active at the concentrations of 0.5 mg/ml and above (SET II). Hence It has been concluded from the foregoing experiments that β-casein isolated from human milk, a recombinant form of the β-casein contained in human milk, and hydrolysates of both, inhibits the attachment of H. influenzae to human cells. Furthermore, inasmuch as H. influenzae have been identified in the literature as being associated with otitis media, it has been concluded that the above identified forms of human β-casein may be employed in the prevention and treatment of otitis media in humans, especially in human infants. In view of the therapeutic effect of enterally ingested human milk, containing human β-casein upon otitis media, it is concluded that the above identified forms of human β-casein have a therapeutic benefit when enterally (orally) ingested.

The therapeutic effects described in the preceding paragraph may be provided by an enteral liquid nutritional product, such as infant formula, comprising one or more proteins not contained in human milk in combination with a therapeutically effective amount of at least one of the forms of human β-casein described in the preceding paragraph. It is further concluded that the attachment of H. influenzae to human oropharyngeal cells may be inhibited by administering via a nasal passageway, or as a throat spray, a formulation containing a therapeutically effective amount of at least one of the forms of human β-casein identified in the preceding paragraph. Such a nasally administered formulation may be in the form of either drops or a spray.

The enteral, throat spray and nasal products and methods are believed to be effective in inhibiting the attachment of H. influenzae to human cells because the interaction of the human β-casein and H. influenzae is believed to occur in the nasopharynx via direct contact rather than following digestion aid absorption of the β-casein.

It is believed that the above identified forms of human β-casein may be incorporated into any standard or specialized enteral liquid nutritional product containing at least one protein not found in human milk, such as bovine milk based or soy based infant formulas, and other beverages consumed by young children. In a preferred embodiment no proteins or hydrolysates thereof found in human milk, other than β-casein, are contained in the liquid enteral nutritional product. Such a product has utility in the treatment and prevention of otitis media in human infants.

While preferred embodiments of the invention have been disclosed, it will be apparent to those skilled in the art that various changes and modifications may be made therein without deviating from the spirit or scope of this invention.

---

We claim:

1. A method of treating *H. influenzae* infection in humans comprising administering, via a nasal passageway, a formulation comprising a therapeutically effective amount of at least one material selected from the group consisting of β-casein isolated from human milk, a recombinant form of the β-casein contained in human milk and hydrolysates of both.

2. A method of treating *H. influenzae* infection in humans comprising administering an oral formulation comprising a therapeutically effective amount of at least one material selected from the group consisting β-casein isolated from human milk, a recombinant form of the β-casein contained in human milk and hydrolysates of both.

3. The method of claim 2, wherein said oral formulation is a throat spray.

4. A method of inhibiting the infection of mammalian cells by *H. influenzae* comprising administering, via a nasal passageway, a formulation comprising a therapeutically effective amount of at least one material selected from the group consisting of β-casein isolated from human milk, a recombinant form of the β-casein contained in human milk and hydrolysates of both.

5. A method of inhibiting the infection of mammalian cells by *H. influenzae* comprising administering an oral formulation comprising a therapeutically effective amount of at least one material selected from the group consisting of β-casein isolated from human milk, a recombinant form of the β-casein contained in human milk and hydrolysates of both.

6. The method of claim 5, wherein said oral formulation is a throat spray.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
    ( A ) LENGTH:1065 base pairs
    ( B ) TYPE:Nucleic acid
    ( C ) STRANDEDNESS: Single
    ( D ) TOPOLOGY: Unknown ( i i ) MOLECULE TYPE: Cloned cDNA representing the product of a human genomic DNA segment.
    ( A ) DESCRIPTION: Human milk 'eta- casein ( i i i ) HYPOTHETICAL:

( i v ) ANTI-SENSE:
    ( v ) FRAGMENT TYPE:

( v i ) ORIGINAL SOURCE: Human
    ( A ) ORGANISM: Homo sapiens
    ( B ) STRAIN:
    ( C ) INDIVIDUAL ISOLATE:
    ( D ) DEVELOPMENTAL STAGE: Adult
    ( E ) HAPLOTYPE:
    ( F ) TISSUE TYPE: Mammary gland
    ( G ) CELL TYPE:
    ( H ) CELL LINE:
      ( I ) ORGANELLE:

( v i i ) IMMEDIATE SOURCE: Human Mammary Gland
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD: DNA sequencing and restriction analysis
    ( D ) OTHER INFORMATION: The encoded product of nucleotide SEQ ID NO:1: is the human milk protein, '-casein.

( x ) PUBLICATION INFORMATION:
    ( A ) AUTHORS: B. Lonnerdal et al
    ( B ) TITLE: Cloning and sequencing of a cDNA encoding human milk beta- casein
    ( C ) JOURNAL:Federation European Biochemical Society Letters
    ( D ) VOLUME:269
    ( E ) ISSUE:
    ( F ) PAGES:153 - 156
    ( G ) DATE:1990
    ( H ) DOCUMENT NUMBER:
      ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 1:

```
CGG  ATG  AAG  GTC  CTC  ATC  CTC  GCC  TGC  CTG  GTG  GCT  CTT  GCT  CTT      45

GCA  AGG  GAG  ACC  ATA  GAA  AGC  CTT  TCA  AGC  AGT  GAG  GAA  TCT  ATT      90
```

| | | | | | | | | | | | | | | |
|---|---|---|---|---|---|---|---|---|---|---|---|---|---|---|
|ACA|GAA|TAC|AAG|AAA|GTT|GAG|AAG|GTT|AAA|CAT|GAG|GAC|CAG|CAG|135|
|CAA|GGA|GAG|GAT|GAA|CAC|CAG|GAT|AAA|ATC|TAC|CCC|TCT|TTC|CAG|180|
|CCA|CAG|CCT|CTG|ATC|TAT|CCA|TTC|GTT|GAA|CCT|ATC|CCC|TAT|GGT|225|
|TTT|CTT|CCA|CAA|AAC|ATT|CTG|CCT|CTT|GCT|CAG|CCT|GCT|GTG|GTG|270|
|CTG|CCT|GTC|CCT|CAG|CCT|GAA|ATA|ATG|GAA|GTC|CCT|AAA|GCT|AAA|315|
|GAC|ACT|GTC|TAC|ACT|AAG|GGC|AGA|GTG|ATG|CCT|GTC|CTT|AAA|TCT|360|
|CCA|ACG|ATA|CCC|TTT|TTT|GAC|CCT|CAA|ATC|CCA|AAA|CTC|ACT|GAT|405|
|CTT|GAA|AAT|CTG|CAT|CTT|CCT|CTG|CCT|CTG|CTC|CAG|CCC|TTG|ATG|450|
|CAG|CAG|GTC|CCT|CAG|CCT|ATT|CCT|CAG|ACT|CTT|GCA|CTT|CCC|CCT|495|
|CAG|CCC|CTG|TGG|TCT|GTT|CCT|CAG|CCC|AAA|GTC|CTG|CCT|ATC|CCC|540|
|CAG|CAA|GTG|GTG|CCC|TAC|CCT|CAG|AGA|GCT|GTG|CCT|GTT|CAA|GCC|585|
|CTT|CTG|CTC|AAC|CAA|GAA|CTT|CTA|CTT|AAC|CCC|ACC|CAC|CAG|ATC|630|
|TAC|CCT|GTG|ACT|CAG|CCA|CTT|GCC|CCA|GTT|CAT|AAC|CCC|ATT|AGT|675|
|GTC|TAA|GAA|GAT|TTC|AAA|GTT|AAT|TTT|CCC|TCC|TTA|TTT|TTG|AAT|720|
|TGA|CTG|AGA|CTG|GAA|ATA|TGA|TGC|CTT|TTC|CGT|CTT|TGT|ATC|ACG|765|
|TTA|CCC|CAA|ATT|AAG|TAT|GTT|TGA|ATG|AGT|TTA|TAT|GGA|AAA|AAT|810|
|GAA|CTT|TGT|CCC|TTT|ATT|TAT|TTT|ATA|TAT|TAT|GTC|ATT|CAT|TTA|855|
|ATT|TGA|AAT|TTG|ACT|CAT|GAA|CTA|TTT|ACA|TTT|TCC|AAA|TCT|TAA|900|
|TTC|AAC|TAG|TAC|CAC|AGA|AGT|TCA|ATA|CTC|ATT|TGG|AAA|TGC|TAC|945|
|AAA|CAT|ATC|AAA|CAT|ATG|TAT|ACA|AAT|TGT|TTC|TGG|AAT|TGT|GCT|990|
|TAT|TTT|TAT|TTC|TTT|AAG|AAT|CTA|TTT|CCT|TTC|CAG|TCA|TTT|CAA|1035|
|TAA|ATT|ATT|CTT|AAG|CAT|AAA|AAA|AAA|AAA| | | | | |1065|

( 2 ) INFORMATION FOR SEQ ID NO: 2:

( i ) SEQUENCE CHARACTERISTICS:
        ( A ) LENGTH:105 base pairs
        ( B ) TYPE:Nucleic acid
        ( C ) STRANDEDNESS: Single
        ( D ) TOPOLOGY: Unknown ( i i ) MOLECULE TYPE: Synthetic oligonucleotide.
        ( A ) DESCRIPTION:

( i i i ) HYPOTHETICAL:

( i v ) ANTI-SENSE:
        ( v ) FRAGMENT TYPE:

( v i ) ORIGINAL SOURCE: Synthetic Oligonucleotide Sequence
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
            ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:

(C) UNITS:

(ix) FEATURE:
    (A) NAME/KEY:
    (B) LOCATION:
    (C) IDENTIFICATION METHOD: DNA sequencing and restriction
        analysis
    (D) OTHER INFORMATION: The synthetic oligonucleotide assures
        adaptation of translation sequence to E. coli codon
        usuage.

(x) PUBLICATION INFORMATION:
    (A) AUTHORS: L. Hansson et al
    (B) TITLE: Expression of Human Milk '-casein in Escherichia
        coli: Comparison of Recombinant Protein with Native
        Isoforms.
    (C) JOURNAL:Protein Expression and Purification
    (D) VOLUME:4
    (E) ISSUE:
    (F) PAGES:373 - 381
    (G) DATE:1993
    (H) DOCUMENT NUMBER:
        (I) FILING DATE:
    (J) PUBLICATION DATE:
    (K) RELEVANT RESIDUES IN SEQ ID NO:

(xi) SEQUENCE DESCRIPTION: SEQ ID NO: 2:

```
CTG CAG AAT TCA TAT GCG TGA AAC CAT CGA ATC CCT GAG CTC GAG      45

CGA AGA ATC GAT CAC CGA ATA CAA AAA AGT TGA AAA AGT TAA ACA      90

CGA GGA CCA GGA TCC                                             105
```

(2) INFORMATION FOR SEQ ID NO: 3:

(i) SEQUENCE CHARACTERISTICS:
        (A) LENGTH:71 base pairs
        (B) TYPE:Nucleic acid
        (C) STRANDEDNESS: Single
        (D) TOPOLOGY: Unknown (ii) MOLECULE TYPE: Synthetic oligonucleotide.
        (A) DESCRIPTION:

(iii) HYPOTHETICAL:

(iv) ANTI-SENSE:
        (v) FRAGMENT TYPE:

(vi) ORIGINAL SOURCE: Synthetic Oligonucleotide Sequence
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
            (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD: DNA sequencing and restriction
            analysis
        (D) OTHER INFORMATION: The synthetic oligonucleotide encodes
            the carboxy- terminal end and translation stop.

(x) PUBLICATION INFORMATION:

(A) AUTHORS: L. Hansson et al
(B) TITLE: Expression of Human Milk '-casein in Escherichia
coli:Comparison of Recombinant Protein with Native
Isoforms.
(C) JOURNAL:Protein Expression and Purification
(D) VOLUME:4
(E) ISSUE:
(F) PAGES:373 - 381
(G) DATE:1993
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 3:

```
AGA TCT ACC CTG TGA CTC AGC CAC TTG CCC CAG TTC ATA ACC CCA    45
TTA GTG TCT AAT AAG GAT CCG AAT TC                             71
```

(2) INFORMATION FOR SEQ ID NO: 4:

(i) SEQUENCE CHARACTERISTICS:
(A) LENGTH:68 base pairs
(B) TYPE:Nucleic acid
(C) STRANDEDNESS: Single
(D) TOPOLOGY: Unknown (ii) MOLECULE TYPE: Synthetic oligonucleotide.
(A) DESCRIPTION:

(iii) HYPOTHETICAL:

(iv) ANTI-SENSE:
(v) FRAGMENT TYPE:

(vi) ORIGINAL SOURCE: Synthetic Oligonucleotide Sequence
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD: DNA sequencing and restriction
analysis
(D) OTHER INFORMATION: Modified enterotoxin STII signal
sequence.

(x) PUBLICATION INFORMATION:
(A) AUTHORS: L. Hansson et al
(B) TITLE: Expression of Human Milk '-casein in Escherichia
coli:Comparison of Recombinant Protein with Native
Isoforms.
(C) JOURNAL:Protein Expression and Purification
(D) VOLUME:4
(E) ISSUE:
(F) PAGES:373 - 381
(G) DATE:1993
(H) DOCUMENT NUMBER:
(I) FILING DATE:
(J) PUBLICATION DATE:
(K) RELEVANT RESIDUES IN SEQ ID NO:

( x i ) SEQUENCE DESCRIPTION: SEQ ID NO: 4:

CAT GAA AAA GAA TAT CGC ATT TCT TCT TGC ATC GAT GTT CGT TTT      45

TTC TAT TGC TAC AAA TGC ATA TG        68

( 2 ) INFORMATION FOR SEQ ID NO: 5:

( i ) SEQUENCE CHARACTERISTICS:
        ( A ) LENGTH:37 base pairs
        ( B ) TYPE:Nucleic acid
        ( C ) STRANDEDNESS: Single
        ( D ) TOPOLOGY: Unknown ( i i ) MOLECULE TYPE: Synthetic oligonucleotide.
        ( A ) DESCRIPTION:

( i i i ) HYPOTHETICAL:

( i v ) ANTI-SENSE:
        ( v ) FRAGMENT TYPE:

( v i ) ORIGINAL SOURCE: Synthetic Oligonucleotide Sequence
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD: DNA sequencing and restriction
            analysis
        ( D ) OTHER INFORMATION:

( x ) PUBLICATION INFORMATION:
        ( A ) AUTHORS: L. Hansson et al
        ( B ) TITLE: Expression of Human Milk '-casein in Escherichia
            coli:Comparison of Recombinant Protein with Native
            Isoforms.
        ( C ) JOURNAL:Protein Expression and Purification
        ( D ) VOLUME:4
        ( E ) ISSUE:
        ( F ) PAGES:373 - 381
        ( G ) DATE:1993
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 5:

CAT ATG CAC GTG AAA CCA TCG AAT CCC TGA GCT CGA G      37